(12) United States Patent
Snady

(10) Patent No.: US 8,211,417 B1
(45) Date of Patent: Jul. 3, 2012

(54) METHOD OF BOWEL CLEANSING

(76) Inventor: Harry Snady, Weehawken, NJ (US)

( * ) Notice: Subject to any disclaimer, the term of this patent is extended or adjusted under 35 U.S.C. 154(b) by 384 days.

(21) Appl. No.: 12/589,979

(22) Filed: Oct. 31, 2009

(51) Int. Cl.
*A61K 33/06* (2006.01)

(52) U.S. Cl. ...................... 424/78.01; 424/682

(58) Field of Classification Search .............. None
See application file for complete search history.

(56) References Cited

U.S. PATENT DOCUMENTS

| | | |
|---|---|---|
| 5,197,950 A | 3/1993 | Clayton |
| 5,616,346 A | 4/1997 | Aronchick |
| 5,670,158 A | 9/1997 | Davis et al. |
| 5,710,183 A | 1/1998 | Halow |
| 5,997,906 A | 12/1999 | Wood et al. |
| 6,162,464 A | 12/2000 | Jacob et al. |
| 7,282,223 B2 * | 10/2007 | Stern .............................. 424/725 |
| 7,291,324 B2 | 11/2007 | Dennett, Jr. et al. |
| 7,684,852 B2 * | 3/2010 | Lefere et al. .................. 600/431 |
| 2006/0024385 A1 * | 2/2006 | Pedersen ....................... 424/725 |
| 2010/0278949 A1 * | 11/2010 | Scott ............................. 424/757 |
| 2011/0288180 A1 * | 11/2011 | Korzenik et al. ............. 514/723 |

* cited by examiner

*Primary Examiner* — Phyllis G. Spivack

(57) ABSTRACT

A method is disclosed for cleansing bowels prior to a colonic procedure utilizing conventional preparations along with potatoes.

1 Claim, No Drawings

METHOD OF BOWEL CLEANSING

BACKGROUND OF THE INVENTION

1. Field of the Invention

The present disclosure involves a new method that can be used to safely and effectively cleanse a patient's bowels, especially the colon prior to diagnostic or surgical procedures.

2. Background Information

Clinical research has shown that early detection of colorectal cancer (CRC) is a high clinical priority. A colon examination has been shown to be useful in detecting early cancer or premalignant polyps. Patients who are undergoing this diagnostic examinations of the large bowel usually undergo preparation to assure that the bowel is cleansed of all fecal material adequately before the procedure. Practitioners agree that colonoscopy detects neoplasms at the highest rate and simultaneously affords the opportunity for their endoscopic removal. Current the cleaning procedures associated with this procedure include the combination of reduced food intake with laxatives, enemas, suppositories, bowel evacuants, or orthograde colonic lavage.

These procedures each have difficulties. In particular, conventional techniques are only effective in 85% of patients because patients cannot tolerate existing preparations. In addition, existing preparations result in suboptimal cleansing and, thus, repeat procedures and/or inaccurate readings of diagnostic procedure results.

BRIEF DESCRIPTION OF THE DRAWINGS

No drawings are necessary to understand the current disclosure.

SUMMARY OF THE INVENTION

A novel method of bowel cleansing in preparation for colonic procedures consisting of a patient consuming only clear fluids a day prior to a colonic procedure, except for potatoes at breakfast; then drinking at least 64 fluid ounces of clear fluids throughout said day, then patient drinking approximately 10 fluid ounces of Magnesium Citrate between 1 p.m. and 5 p.m. on said day; then drinking between 25 and 33 grams of P-glycol approximately two hours thereafter; then approximately 8 fluid ounces of water or clear fluid about ten minutes thereafter; then drinking approximately 10 fluid ounces of Magnesium Citrate between two or three hours thereafter; then drinking another 25 to 33 grams of P-glycol as at a time certain prior to the colonic procedure; and finally refraining from consumption of all fluids approximately four hours prior to said colonic procedures.

DETAILED DESCRIPTION

The current disclosure utilizes commercially available products in a novel combination that achieves optimal results. The specific products utilized are 20 fluid ounces (two 10 fl oz bottles) of Citrate magnesia (laxative), between 50 and 66 grams of polyethylene glycol (P-glycol) powder, and a standardized saline enema product such as Fleets enema. These are commonly available without a prescription as over the counter medications. This disclosure teaches combining these products in specific amounts and administering them in a specific order to be used for cleansing of the colon for preparation for colonoscopy. The novel mixture must be administered in conjunction with specific foods, both to eat and avoid. The mixture replaces other currently employed preparation medications or use of the Citrate or P-glycol powder alone. The novel mixture combined with the protocol disclosed herein allows patients to achieve adequate cleansing without the drawbacks noted above.

The following description, for purposes of explanation, specific numbers, materials and configurations are set forth in order to provide a thorough understanding of the present invention. However, it will be apparent to one skilled in the art that the present invention may be practiced without the specific details. In other instances, well known features are omitted or simplified in order not to obscure the present invention. Furthermore, for ease of understanding, certain method steps are delineated as separate steps, however, these separately delineated steps should not be construed as necessarily order dependent in their performance.

In the preferred method begins the day prior to the diagnostic or surgical procedure. The patient must consume clear fluids in abundance, preferably at least 64 fluid ounces. Conventional precautions associated with colonoscopy preparation are observed, including but not limited to avoidance of red or purple fluids (e.g., grape juice) which may be mistaken for blood.

The patient must refrain from consuming all solid foods, with the sole exception of this method of consuming potatoes. In particular, patients should consume two to three medium boiled potatoes, preferably peeled with butter and a little salt as desired, for breakfast the day prior to the procedure. The method requires that no further solid food be consumed following the potatoes.

Between 1 p.m. and 5 p.m. the same day, the patient must perform the following protocol. First, drink approximately 10 fl. oz. of Magnesium Citrate while continuing to drink clear fluids.

Second, approximately two hours later, the patient drinks one dosage of between 25 and 33 grams of P-glycol. This may be mixed with a clear beverage of the patient's preference, such as tea or Gatorade.

Third, about ten minutes following the consumption of the P-Glycol dose in the second step, the patient consumes a full glass (approx. 8 fl. oz.) of water or other clear fluid.

Fourth, two or three hours following the consumption of the water or fluid of the third step, the patient drinks a second, approximate 10 fl. oz. dose of Magnesium Citrate. s better than existing because it results in better cleansing and is less costly to the patient.

Fifth, the patient continues drinking clear fluids throughout the day, as desired by the patient Sixth, if the procedure is to be performed the following morning, the patient drinks another 25 to 33 grams of P-glycol between approximately 9 p.m. and 11 p.m. Alternatively, for an afternoon procedure the following day, the patient drinks the second 25 to 33 grams of P-glycol at approximately 8 a.m. of the day of the afternoon procedure.

Seventh, starting at approximately four hours before the diagnostic or surgical procedure, the patient must refrain from consuming all fluids. The sole exception is a sip of water sufficient to ingest any medications.

Thus, a method for optimal bowel cleansing has been described.

What is claimed is:

1. A method of cleansing bowels in a patient a day prior to a colonic procedure, comprising the steps:
   a. wherein said patient consumes only clear fluids, except for potatoes at breakfast;
   b. wherein said patient drinks at least 64 fluid ounces of clear fluids throughout said day;

c. wherein said patient drinks approximately 10 fluid ounces of magnesium citrate between 1 p.m. and 5 p.m. on said day;
d. wherein said patient drinks between 25 and 33 grams of polyethylene-glycol approximately two hours after the magnesium citrate;
e. wherein said patient drinks approximately 8 fluid ounces of water or clear fluid about ten minutes after the polyethylene-glycol;
f. wherein said patient drinks approximately 10 fluid ounces of magnesium citrate between two or three hours after the water or clear fluid;
g. wherein said patient drinks another 25 to 33 grams of polyethylene-glycol at a time between four to eight hours prior to said procedure
h. wherein said patient refrains from consuming all fluids approximately four hours prior to said procedure.

* * * * *